United States Patent
Searle et al.

(10) Patent No.: US 11,617,829 B2
(45) Date of Patent: *Apr. 4, 2023

(54) INFUSION SYSTEMS

(71) Applicant: Becton, Dickinson and Company, Franklin Lakes, NJ (US)

(72) Inventors: Gary M. Searle, Norfolk, MA (US); Charles G. Hwang, Wellesley, MA (US)

(73) Assignee: BECTON, DICKINSON AND COMPANY, Franklin Lakes, NJ (US)

(*) Notice: Subject to any disclaimer, the term of this patent is extended or adjusted under 35 U.S.C. 154(b) by 351 days.

This patent is subject to a terminal disclaimer.

(21) Appl. No.: 16/825,599

(22) Filed: Mar. 20, 2020

(65) Prior Publication Data
US 2020/0215264 A1    Jul. 9, 2020

Related U.S. Application Data

(62) Division of application No. 16/145,667, filed on Sep. 28, 2018, now Pat. No. 10,773,019, which is a
(Continued)

(51) Int. Cl.
*A61M 5/162* (2006.01)
*A61M 5/142* (2006.01)
(Continued)

(52) U.S. Cl.
CPC ........ *A61M 5/162* (2013.01); *A61M 5/14216* (2013.01); *A61M 5/14228* (2013.01);
(Continued)

(58) Field of Classification Search
CPC .............. A61M 5/162; A61M 5/14216; A61M 5/14228; A61M 5/14244; A61M 5/14248;
(Continued)

(56) References Cited

U.S. PATENT DOCUMENTS

| 2,768,623 A | 10/1956 | Marchand |
| 3,834,380 A | 9/1974 | Boyd |

(Continued)

FOREIGN PATENT DOCUMENTS

| FR | 2784586 A1 | 4/2000 |
| JP | 2001523484 A | 11/2001 |

(Continued)

*Primary Examiner* — Tiffany Legette
(74) *Attorney, Agent, or Firm* — Dickinson Wright PLLC

(57) ABSTRACT

An infusion system comprises an infusion set (30) with one or more advanced features including tube set strain relief (10), infusion pumps having heat exchange abilities and two-direction pumping abilities (100), Piezo pump devices (200), reservoirs (220, 240) made from expanded tubing, and oil impregnated pump plungers (302). An exemplary strain relief (10) includes an adhesive layer (12) such as pressure sensitive adhesive (PSA) secured to a base (14). The base (14) rotatably receives a pin (18) of a tube holder (16). The pin (18) is captured within an opening (22) of the base (14) to allow 360 degree rotation of the tube holder (16).

8 Claims, 14 Drawing Sheets

Related U.S. Application Data division of application No. 13/984,023, filed as application No. PCT/US2012/000070 on Feb. 8, 2012, now Pat. No. 10,130,761.

(60) Provisional application No. 61/441,278, filed on Feb. 9, 2011.

(51) Int. Cl.
  *A61M 5/152* (2006.01)
  *A61M 25/00* (2006.01)
  *A61M 25/02* (2006.01)
  *A61M 37/00* (2006.01)
  *A61M 5/44* (2006.01)
  *A61M 39/08* (2006.01)

(52) U.S. Cl.
  CPC .... *A61M 5/14244* (2013.01); *A61M 5/14248* (2013.01); *A61M 5/152* (2013.01); *A61M 25/0023* (2013.01); *A61M 25/02* (2013.01); *A61M 37/0092* (2013.01); *A61M 5/44* (2013.01); *A61M 39/08* (2013.01); *A61M 2205/0222* (2013.01)

(58) Field of Classification Search
  CPC ... A61M 25/02; A61M 25/0023; A61M 39/08
  See application file for complete search history.

(56) References Cited

U.S. PATENT DOCUMENTS

| | | | |
|---|---|---|---|
| 4,025,015 A | 5/1977 | Kolic | |
| 4,972,969 A | 11/1990 | Randklev | |
| 5,353,691 A | 10/1994 | Haber et al. | |
| 5,354,282 A | 10/1994 | Bierman | |
| 5,944,696 A | 8/1999 | Bayless et al. | |
| 6,158,621 A | 12/2000 | Keller | |
| 6,290,676 B1 | 9/2001 | Bierman | |
| 2003/0083621 A1 | 5/2003 | Shaw et al. | |
| 2006/0293640 A1 | 12/2006 | Greco | |
| 2007/0060874 A1 | 3/2007 | Nesbitt et al. | |
| 2007/0066958 A1 | 3/2007 | Wright | |
| 2008/0103483 A1* | 5/2008 | Johnson | A61M 25/008 604/524 |
| 2008/0171993 A1 | 7/2008 | Beran | |
| 2008/0200880 A1 | 8/2008 | Kyvik et al. | |
| 2008/0215006 A1 | 9/2008 | Thorkild | |
| 2008/0221526 A1 | 9/2008 | Fleischer | |
| 2009/0069787 A1 | 3/2009 | Estes et al. | |
| 2009/0076453 A1* | 3/2009 | Mejlhede | A61M 5/14248 604/151 |
| 2009/0198191 A1 | 8/2009 | Chong et al. | |
| 2009/0221971 A1 | 9/2009 | Mejlhede et al. | |
| 2009/0240201 A1* | 9/2009 | Rotem | A61M 5/142 604/151 |
| 2010/0049128 A1 | 2/2010 | McKenzie et al. | |
| 2010/0286512 A1* | 11/2010 | Dhawale | G21F 5/018 600/431 |

FOREIGN PATENT DOCUMENTS

| | | |
|---|---|---|
| JP | 2002239003 A | 8/2002 |
| JP | 200521459 | 1/2005 |
| JP | 2005507716 A | 3/2005 |
| JP | 2005514095 | 5/2005 |
| JP | 2009240790 | 10/2009 |
| JP | 2009-538692 A2 | 11/2009 |
| JP | 2009538692 | 11/2009 |
| WO | WO-9933504 A1 | 7/1999 |
| WO | 2007/142868 A2 | 12/2007 |
| WO | WO-2010004206 | 1/2010 |
| WO | WO-2010022069 A2 | 2/2010 |
| WO | WO-2010085338 A1 | 7/2010 |
| WO | WO-2010145771 A | 12/2010 |

* cited by examiner

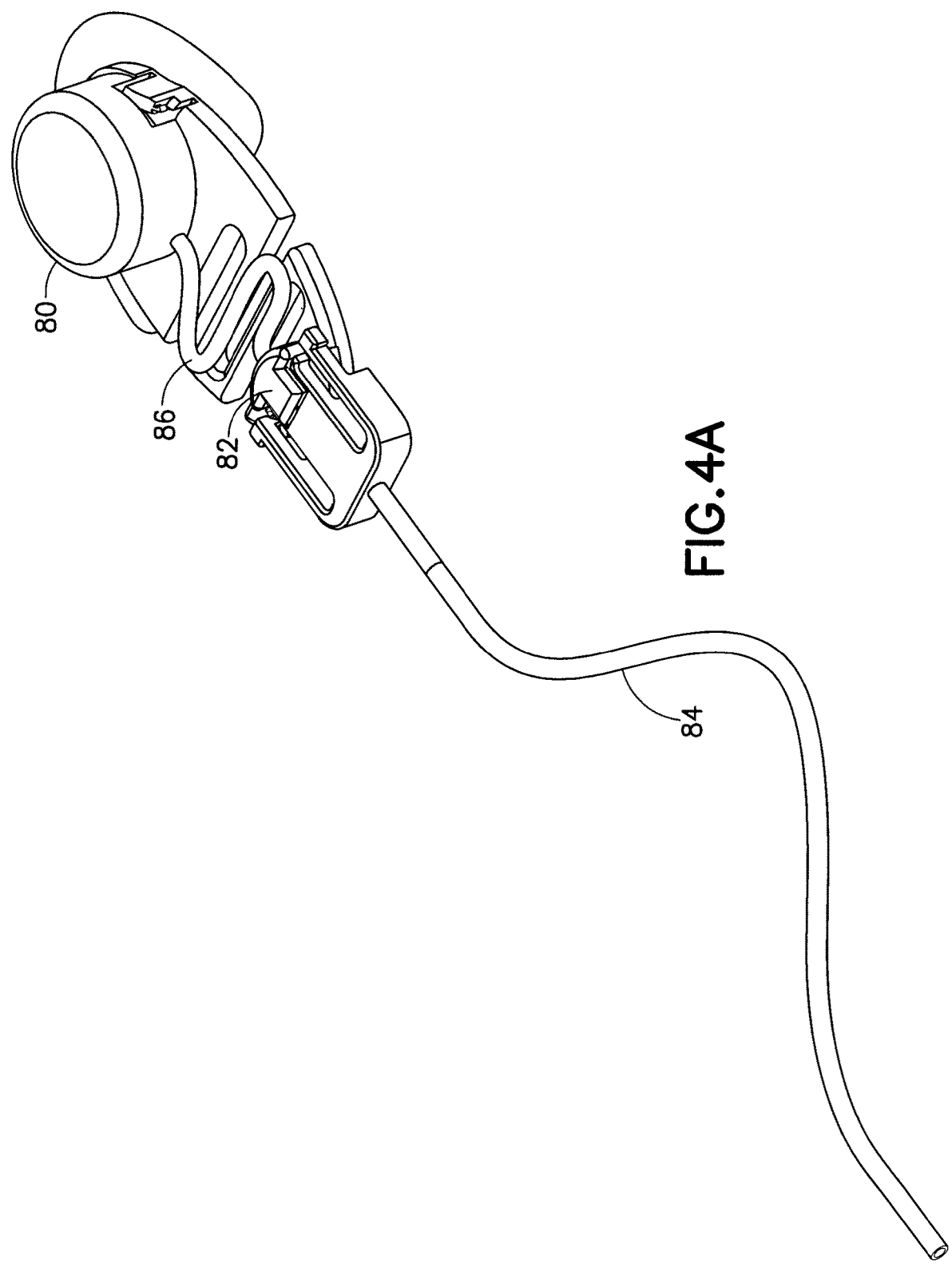

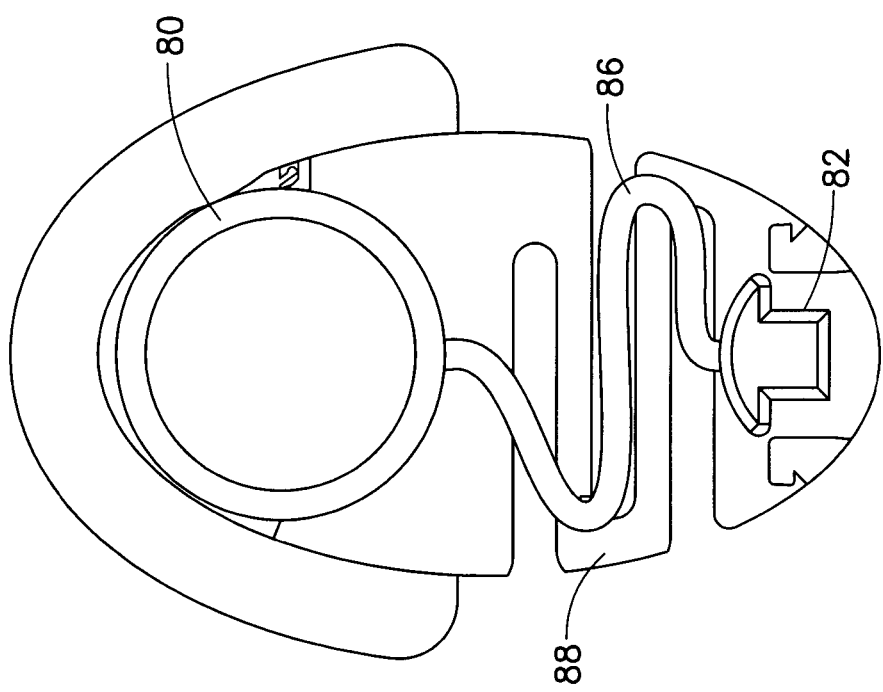

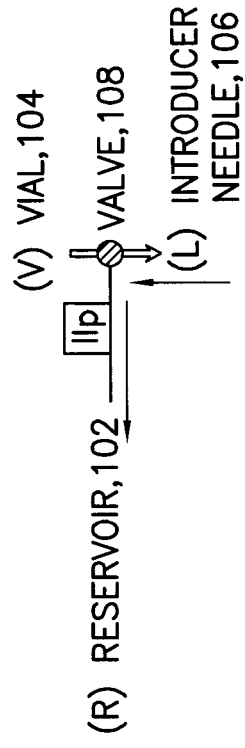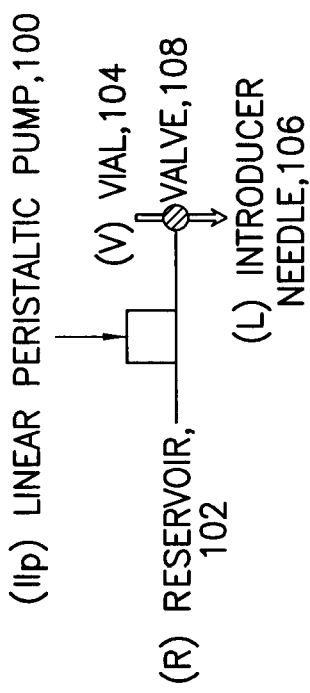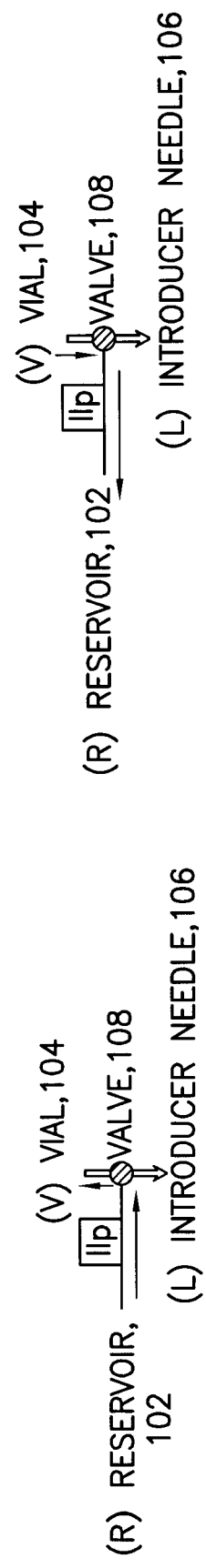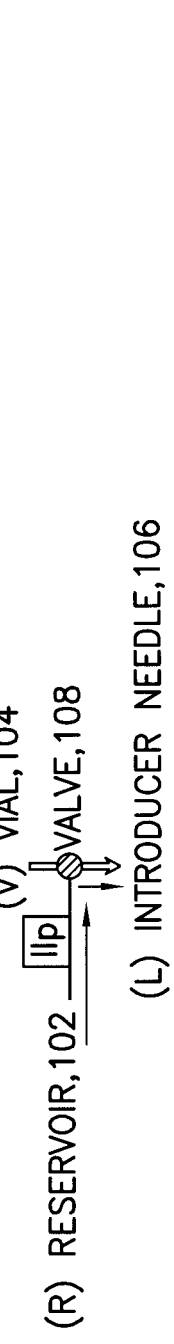

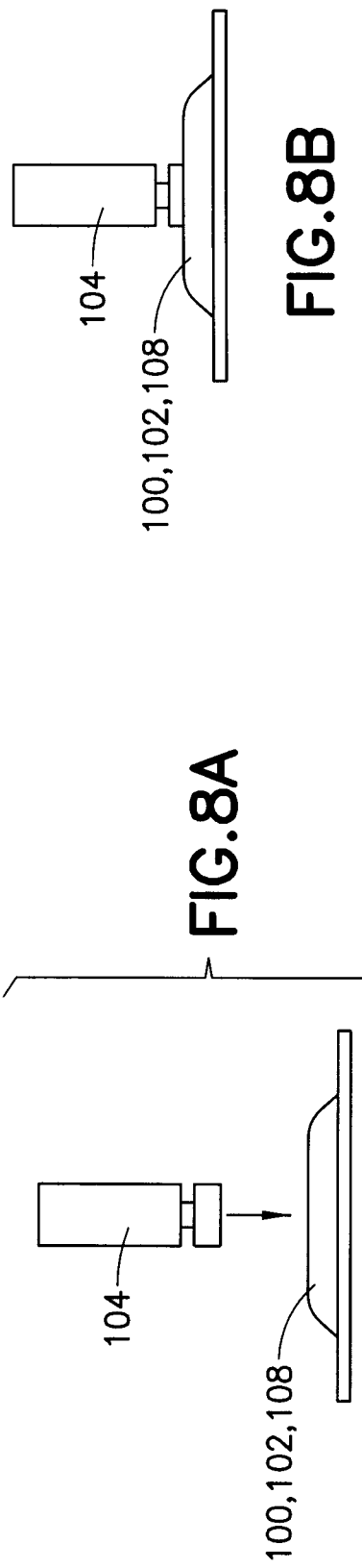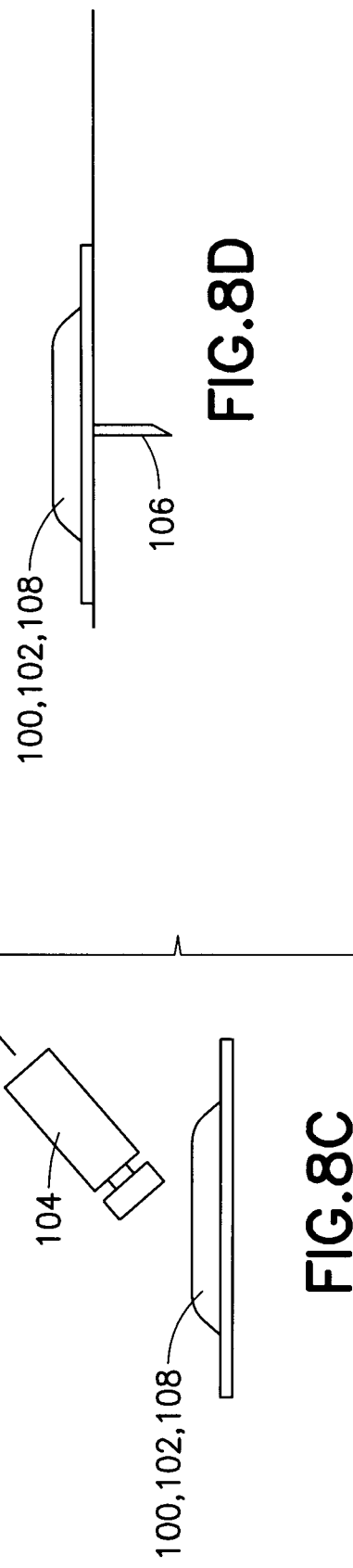

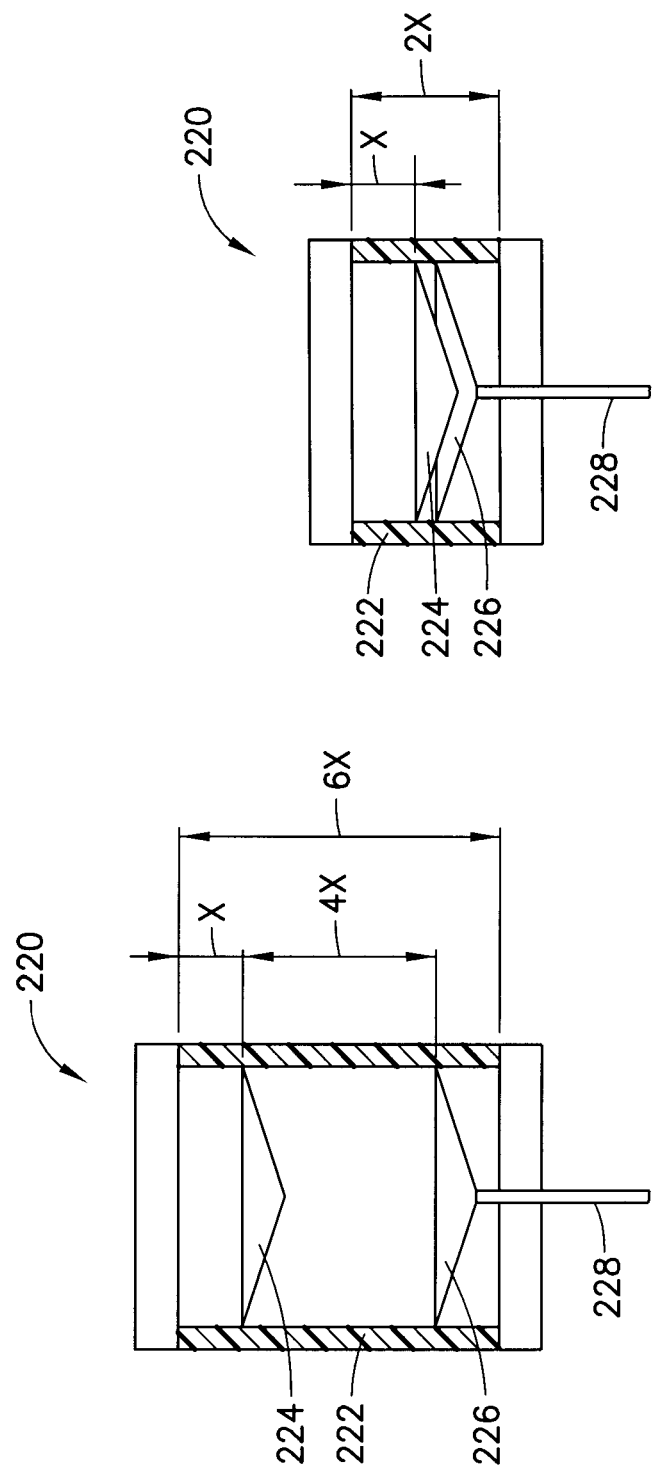

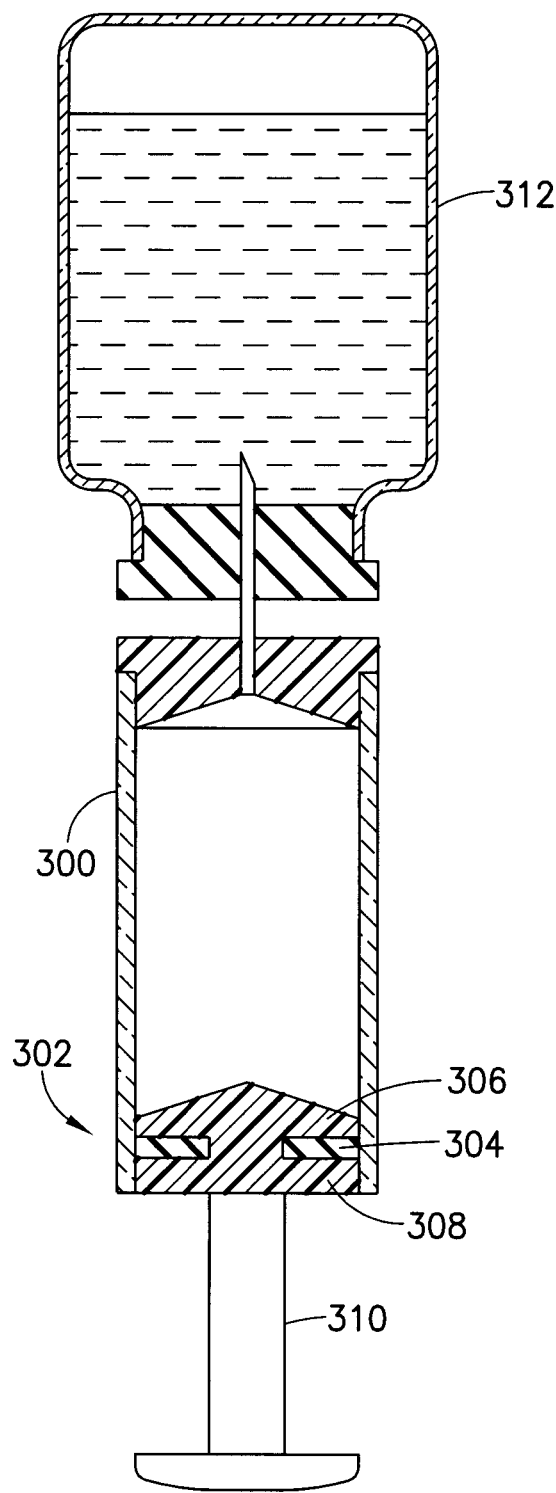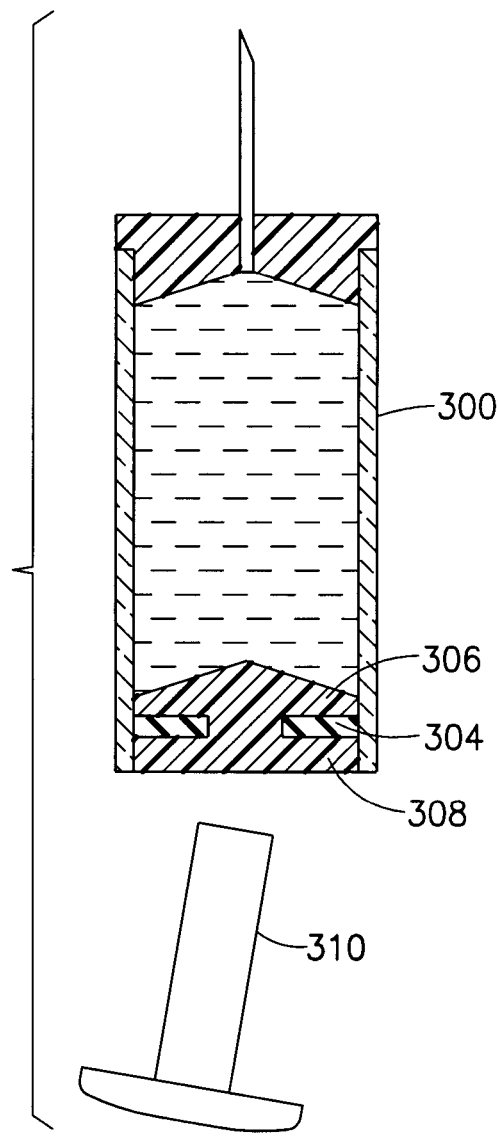
FIG.12A
FIG.12B

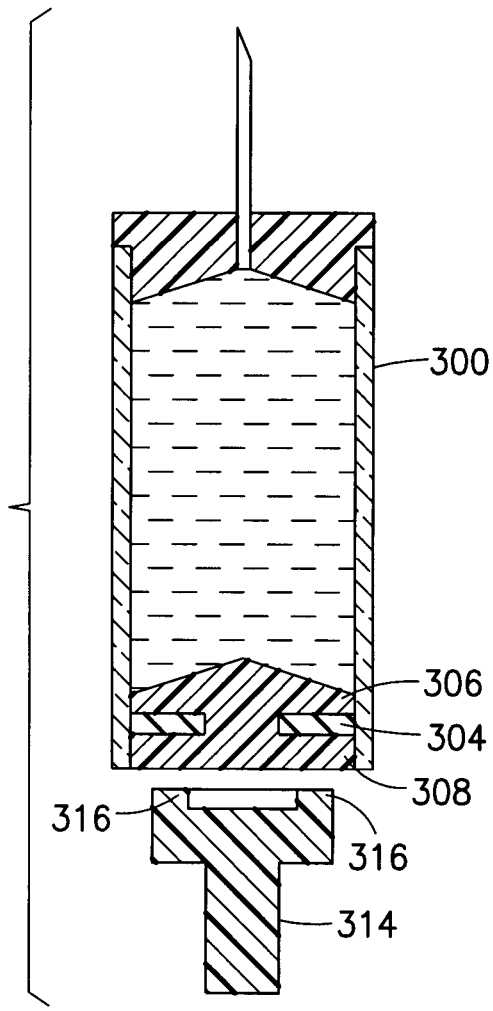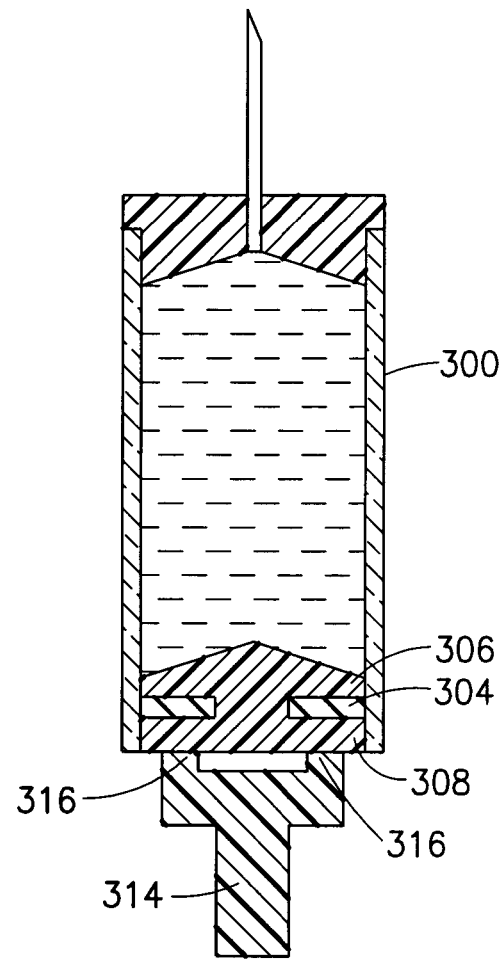
FIG.12C
FIG.12D

INFUSION SYSTEMS

CROSS-REFERENCE TO RELATED APPLICATIONS

This application is a division of U.S. patent application Ser. No. 16/145,667, filed Sep. 28, 2018, which is a division of U.S. patent application Ser. No. 13/984,023, filed Oct. 16, 2013, which claims the benefit under 35 U.S.C. 119(e) of a U.S. provisional patent application of Gary M. Searle et al. entitled "Concepts for Infusion Set Strain Relief, an Oil Impregnated Plunger, a Reservoir Made from Expanded Tubing, and Piezo Pump Devices", Ser. No. 61/441,278, filed Feb. 9, 2011, the entire contents of each are hereby incorporated by reference.

FIELD OF THE INVENTION

The present invention relates generally to components and elements of infusion systems, specifically an infusion set with one or more features including tube set strain relief, infusion pumps having heat exchange abilities, oil impregnated plungers, two-direction pumping abilities, Piezo pump devices, and reservoirs made from expanded tubing.

BACKGROUND OF THE INVENTION

A large number of people suffering from diabetes use some form of daily insulin therapy to maintain close control of their glucose levels. Currently, there are two principal modes of daily insulin therapy. The first mode includes syringes and insulin pens. These devices are simple to use and are relatively low in cost, but they require a needle stick at each injection, typically three to four times per day. The second mode includes infusion pump therapy, which entails the purchase of an insulin pump that lasts for about three years. The initial cost of the pump can be significant, but from a user perspective, the overwhelming majority of patients who have used pumps prefer to remain with pumps for the rest of their lives. This is because infusion pumps, although more complex than syringes and pens, offer the advantages of continuous infusion of insulin, precision dosing and programmable delivery schedules. This results in closer blood glucose control and an improved feeling of wellness.

An infusion pump is but one part of an assembly of infusion elements, which work together to deliver insulin or other medicament to an infusion site. Some elements are disposable, such as the infusion set or pump set which conveys the insulin from a reservoir within the pump into the skin of the user. An infusion set typically consists of a pump connector, a length of tubing, and a hub or base from which an infusion needle, flexible cannula or catheter extends. The hub or base has an adhesive which retains the base of the set on the skin surface during use, which may be applied to the skin manually or with the aid of a manual or automatic insertion device.

As noted above, infusion sets allow diabetic patients to infuse insulin via an infusion pump. To do so, infusion sets use one or more of an infusion needle, flexible cannula or catheter. For example, a steel infusion needle can be used to infuse insulin under the skin surface, either into the subcutaneous or intradermal skin layers, but may irritate the insertion site if moved. Alternatively, a soft, Teflon-based catheter can be provided with the infusion set to infuse insulin under the skin surface, usually into the subcutaneous skin layer, and is associated with less irritation than a steel cannula. However, soft cannulas or catheters are prone to kink which can delay or interrupt the insulin delivery and reduce therapy.

Most soft cannula or catheter infusion sets are inserted using another commonly associated element of infusion sets, a steel introducer needle that is positioned inside the catheter lumen and which extends beyond the catheter to initiate penetration. At insertion and placement, the introducer needle and catheter are both inserted into the infusion site either concurrently with or subsequent to adhesive placement of the infusion set to the skin surface. The introducer needle is then removed from the catheter after penetration, leaving the catheter in place.

Some infusion sets also provide and use a separate spring-loaded inserter that propels the infusion set and/or the introducer needle and catheter into the tissue at a desired speed and to a desired depth. Many such spring-loaded inserters further provide features to automatically retract or shield the introducer needle. Once in place, an infusion set is typically attached to a medicament supply using still another element, such as a length of tubing, which can be subject to inference and adversely affect the infusion set.

Accordingly, each element of the infusion set needs to operate separately and in combination, in an optimal manner. Otherwise, the performance of the infusion set can be adversely affected through the poor performance of individual elements of the infusion set.

SUMMARY OF THE INVENTION

An object of the present invention is to substantially address the above and other concerns, and provide advanced, improved, and novel components and elements of infusion systems that further provide simplicity in manufacture and improvements in use for both insulin and non-insulin applications.

Another object of the present invention is to provide an infusion system for containing and placing an introducer needle, infusion needle, flexible cannula or catheter, an infusion set or other skin contacting element including strain relief features for tube set connections and which avoid the transmission of movement to the introducer needle, infusion needle, flexible cannula or catheter.

Another object of the present invention is to provide an infusion system for containing and placing an introducer needle, infusion needle, flexible cannula or catheter, an infusion set or other skin contacting element including tubing recoiler features for managing the tubing of the tube set connection.

Another object of the present invention is to provide an infusion system for containing and placing an introducer needle, infusion needle, flexible cannula or catheter, an infusion set or other skin contacting element including an expandable and collapsible reservoir, and incorporating such expansion and collapse into the operation of the infusion set.

Another object of the present invention is to provide an infusion pump for use with an infusion system, wherein the pump is configured to operate in both a forward and reverse direction, and incorporating such forward and reverse direction into the operation of the infusion set.

Another object of the present invention is to provide an infusion pump for use with an infusion system, wherein the pump is configured to incorporate a Piezo device, and incorporating such Piezo operation into the operation of the infusion set.

Another object of the present invention is to provide an infusion pump for use with an infusion system, wherein the pump is configured to incorporate a heat exchanger to maintain, cool or heat contents or components of the pump.

Another object of the present invention is to provide an infusion pump for use with an infusion system, wherein the pump is configured to incorporate an oil impregnated plunger, and incorporating such an oil impregnated plunger into the operation of the infusion set.

These and other objects are substantially achieved by providing components and elements of infusion systems, including infusion sets with one or more features including tube set strain relief, infusion pumps having heat exchange abilities, oil impregnated plungers, two-direction pumping abilities, and Piezo devices, and reservoirs made from expanded tubing, and incorporating such features into the operation of the infusion set.

BRIEF DESCRIPTION OF THE DRAWINGS

The various objects, advantages and novel features of the exemplary embodiments of the present invention will be more readily appreciated from the following detailed description when read in conjunction with the appended drawings, in which:

FIGS. 4A and 4B are perspective views of an exemplary integrated strain relief in accordance with an embodiment of the present invention;

FIGS. 7A to 7E are block diagrams of an infusion system incorporating a linear peristaltic pump that can be used to deliver insulin or other medicament to an infusion site in accordance with an embodiment of the present invention;

FIGS. 8A to 8D are perspective views of the infusion system of FIGS. 7A to 7E that can be used to deliver insulin or other medicament to an infusion site in accordance with an embodiment of the present invention;

FIGS. 10A and 10B are views of a tube element that can be used to deliver insulin or other medicament to an infusion site in accordance with an embodiment of the present invention;

FIGS. 12A to 12D are views of another element that can be used to deliver insulin or other medicament to an infusion site in accordance with an embodiment of the present invention.

Throughout the drawings, like reference numerals will be understood to refer to like parts, components and structures.

DETAILED DESCRIPTION OF THE EXEMPLARY EMBODIMENTS

The exemplary embodiments of the present invention described below provide novel means of delivering insulin via an infusion set with one or more advanced features including tube set strain relief, infusion pumps having heat exchange abilities, oil impregnated plungers, two-direction pumping abilities, Piezo pump devices, and reservoirs made from expanded tubing.

Figure 1A:
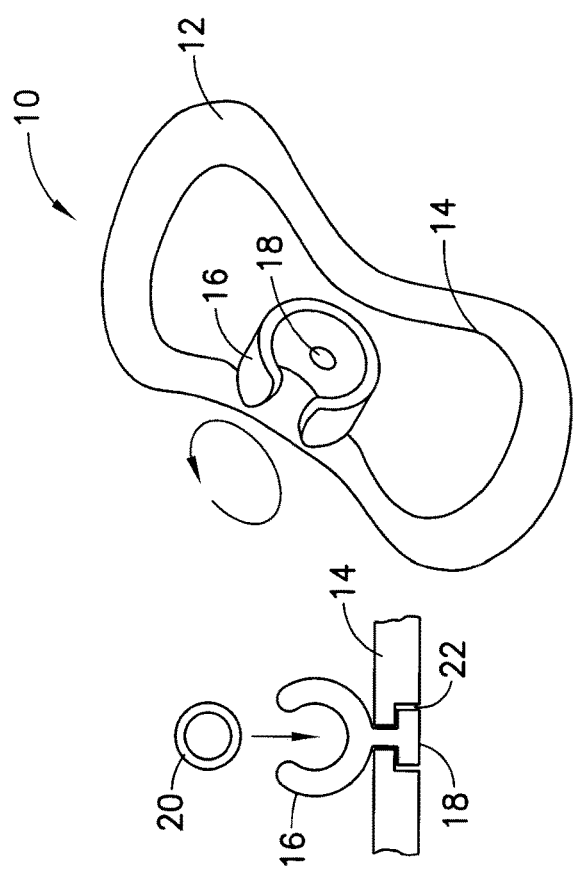
FIGS. 1A to 1C are perspective views of an exemplary universal strain relief in accordance with an embodiment of the present invention.
Figure 1B:
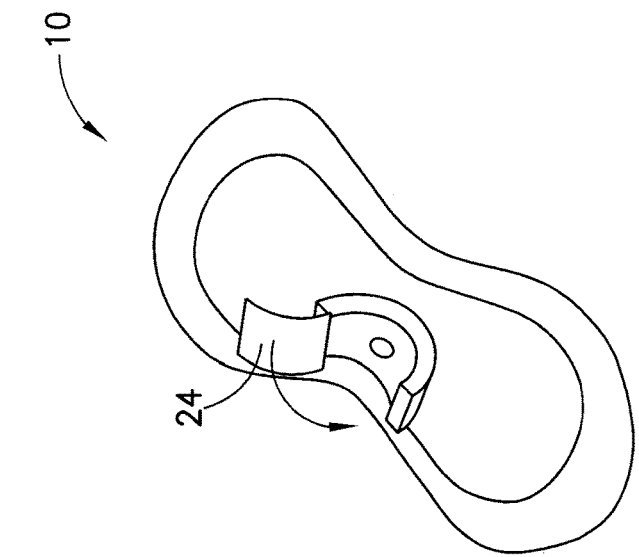
Figure 1C:
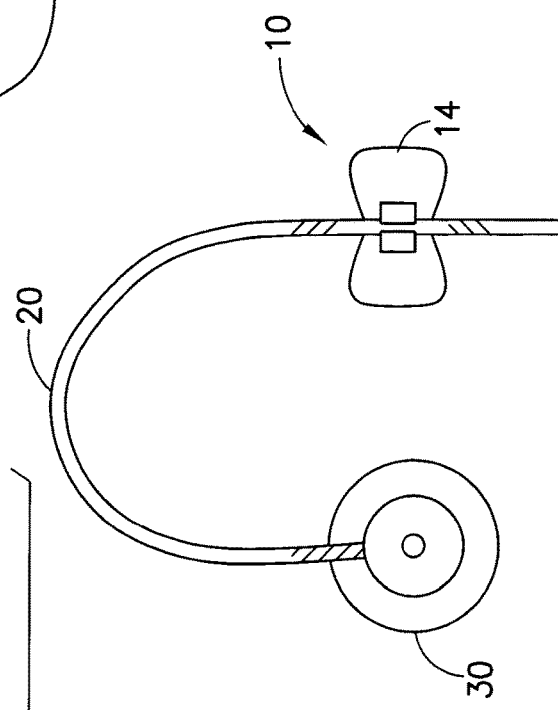

In these and other infusion systems, the use of a strain relief can benefit a user in a number of ways, including the extension of the useful life of an infusion set by reducing or eliminating the micro-motion of the catheter caused by movement or tugging of the line set. Further, by eliminating the influence of line set tugging, such provision of a strain relief can ultimately eliminate tunneling or leakage at the infusion site. Accordingly, an exemplary embodiment of the present invention incorporates a strain relief device into an infusion set, and inserter device, or both. FIGS. 1A to 1C are perspective views of an exemplary universal strain relief in accordance with an embodiment of the present invention.

In FIG. 1A, a universal strain relief 10 is shown, including an enlarged illustration of the assembly with a tube 20 of a set 30. In the exemplary embodiment shown in FIG. 1A, the strain relief 10 comprises an adhesive layer 12 such as pressure sensitive adhesive (PSA) secured to a base 14. The base 14 rotatably receives a pin 18 of a tube holder 16. As shown in the enlargement of FIG. 1A, the pin 18 is captured within an opening 22 of the base 14 to allow 360 degree rotation of the tube holder 16. The tube holder 16 can comprise a circular segment of flexible material with an open portion to allow insertion of the tube. The circular segment can be configured to deflect into an open position upon receiving the tube, and contract to a position to secure the tube once the tube is in position. An adhesive liner can also be provided to cover the adhesive layer 12.

In an exemplary use, a user first removes the adhesive liner from the lower surface to expose the adhesive layer of the bottom of the device 10. The device 10 is then secured near an infusion site, infusion pump, or therebetween, using the exposed adhesive layer. This ensures that the device 10 is fully contacting and adhesively secured to the skin surface. The user then presses the tube 20 of the tube set into the tube holder 16 as shown in FIG. 1C.

The tube holder can further comprise an adhesive tab 24 as shown in FIG. 1B that can be used to hold the tube to the tube holder. In an exemplary use, a user first removes the adhesive liner from the lower surface to expose the adhesive layer of the bottom of the device 10. The device 10 is then secured near an infusion site, infusion pump, or therebetween, using the exposed adhesive layer as discussed above. The user then presses the tube 20 of the tube set into the tube holder and removes the adhesive liner from the adhesive tab 24 which is then placed over the tube and the opening of the tube holder.

Figure 2A:
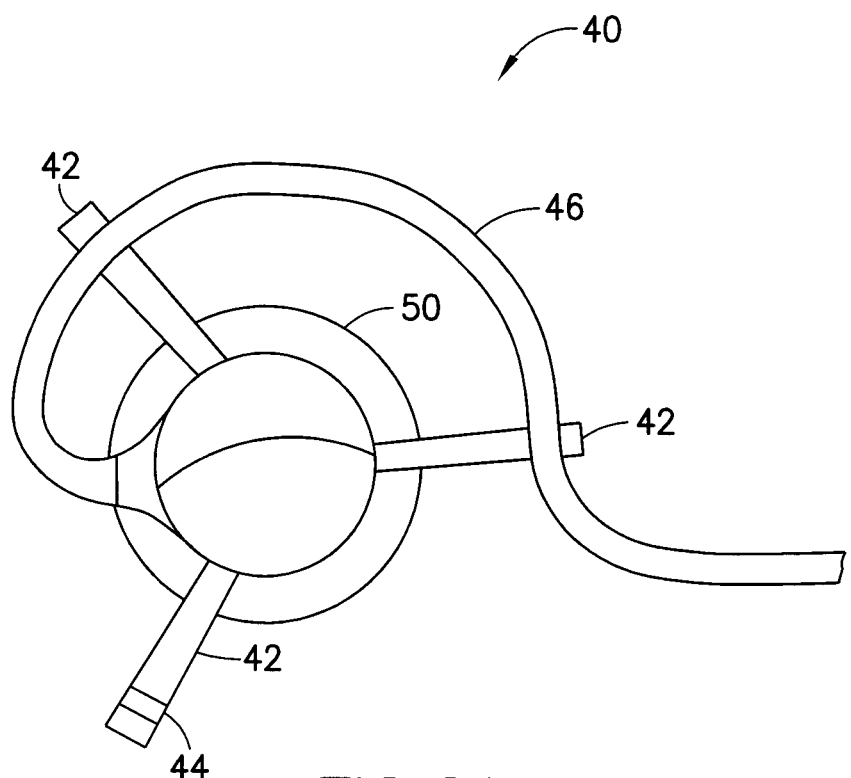
FIGS. 2A and 2B are perspective views of an exemplary integrated spoke design strain relief in accordance with an embodiment of the present invention.
Figure 2B:
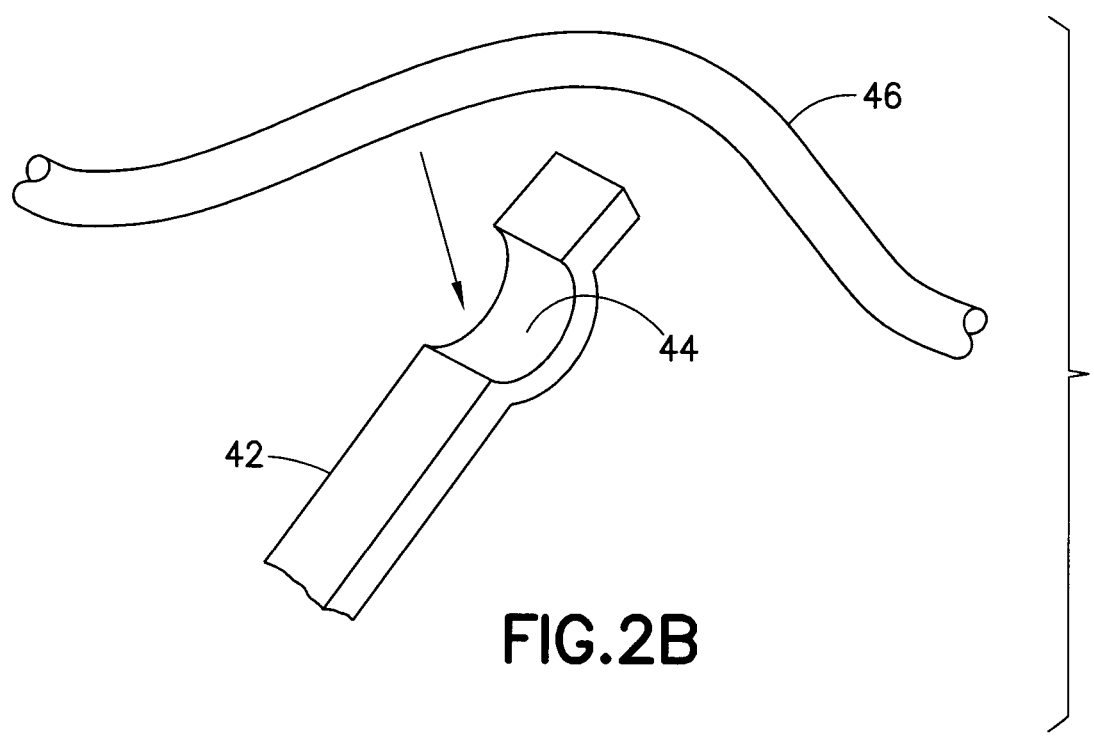

The strain relief 10 of FIGS. 1A to 1C is universal in that it can be used with any set or infusion pump, any tube configuration, and provide 360 degree rotation of the tube. The strain relief 10 can also be used to hold a strain relief loop in place for any set. In yet other embodiments of the present invention, the strain relief device 10 can be integrated into the infusion set. FIGS. 2A and 2B are perspective views of another strain relief incorporated with the infusion set in accordance with an embodiment of the present invention.

In FIGS. 2A and 2B, an exemplary integrated, spoke-design strain relief 40 is shown, including an enlarged illustration of the assembly with a tube 46 of an infusion set 50. In the exemplary embodiment shown, the strain relief 40 comprises one or more flexible arms 42 secured to a set 50 in a spoke-design pattern. Each arm 42 comprises a slot 44 for securing the tubing 46. Specifically, the slot 44 can comprise a circular segment of flexible material with an open portion to allow insertion of the tube. The circular segment can be configured to deflect into an open position upon receiving the tube, and contract to a position to secure the tube once the tube is in position. The slot can further comprise an adhesive tab (not shown) that can be used to hold the tube to the slot substantially as described it the embodiment above.

Figure 3A:
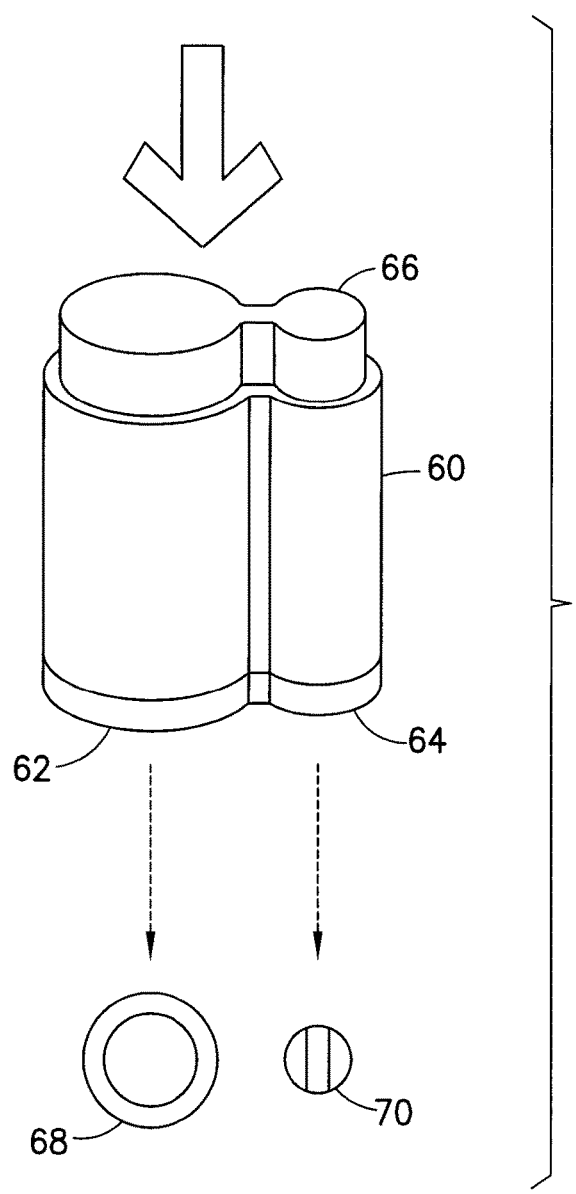
FIGS. 3A to 3C are perspective views of an exemplary universal, inserter-placed strain relief in accordance with an embodiment of the present invention.
Figure 3B:
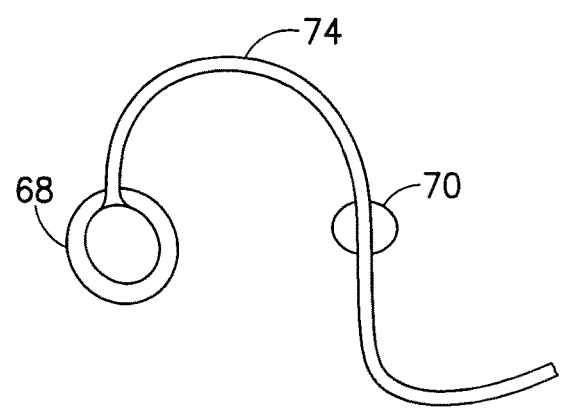
Figure 3C:
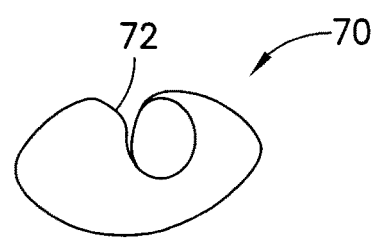

In an exemplary use, a user first places the infusion set 50 at an infusion site. The user then forms a loop of tubing and presses portions of the tubing loop into each slot 44 of each arm 42. As shown in the enlargement of FIG. 2B, the tubing 46 is snapped into the slots 44 of the arms 42 which then hold the tube 46 while providing strain relief. In this embodiment, no additional elements are required as the strain relief element is incorporated with the infusion set. The ability to combine such elements, either integrated with one another, stored with one another, or installed with one another, can simplify use. For example, an inserter can be configured to place both the infusion set and the strain relief, in a single motion. FIGS. 3A to 3C are perspective views of an exemplary universal, inserter-placed strain relief in accordance with an embodiment of the present invention.

In FIGS. 3A to 3C, an exemplary inserter 60 is shown having an infusion set placement opening 62 and a strain relief placement opening 64 within a single housing. The housing of the inserter 60 contains therein the infusion set and strain relief elements at a distal end, and a single user push button 66 at a proximal end. Both elements can be contained therein and covered with an adhesive layer and layer cover (not shown). One or more push buttons 66 can be provided to activate the inserter and simultaneously place the set 68 and the strain relief 70, which can be separate elements as shown in FIG. 3A, or integrally formed in yet other embodiments of the present invention as shown in FIG. 4B described below. In doing so, a single user action can be used to place both the set 68 and the strain relief 70 at an insertion site, without requiring separate user actions. The infusion set and strain relief can share a common adhesive base (not shown) for installation, or can be provided with separate adhesive bases.

An exemplary strain relief 70 is shown in FIG. 3C including an illustration of the assembly with a tube 74 of a set 68 in FIG. 3B. In the exemplary embodiment shown in FIG. 3C, the strain relief 70 comprises a patch having a raised feature and one or more flexible openings or detents 72 for the tubing 74 to snap into. Specifically, the flexible openings or detents 72 can comprise a circular opening of flexible material with an open portion to allow insertion of the tube. The circular opening can be configured to deflect into an open position upon receiving the tube, and contract to a position to secure the tube once the tube is in position. The opening can further comprise an adhesive tab (not shown) that can be used to hold the tube to the opening substantially as described it the embodiments above. As shown in FIG. 3B the tubing 74 is snapped into the opening 72 to hold the tube while providing strain relief.

In an exemplary use, a user first grips the inserter 60 and places the distal end of the inserter against a skin surface. The user can then press the single button 66 to automatically place both the infusion set 68 at an infusion site, and place the strain relief 70 at a position near the infusion set 68. The user then forms a loop of tubing and presses a portion of the tubing loop into the flexible openings or detents 72 of the strain relief 70. In this embodiment, no additional elements are required as the strain relief element is packaged with the infusion set within the inserter 60. In other exemplary embodiments, the strain relief element can be incorporated with the infusion set. Such an exemplary strain relief element incorporated with an infusion set is shown in FIGS. 4A and 4B, which are perspective views of another integrated strain relief in accordance with an embodiment of the present invention.

In FIG. 4A, a low-profile infusion set 80 is shown as placed with a tube set connection element 82 integrated with, but isolated from, the infusion set 80. Specifically, as shown in FIG. 4B, the infusion set 80 and the tube set connection element 82 are coupled via a tortuous pathed or zigzag patterned portion of a base 88 (with or without adhesive), and a similarly patterned portion of tubing 86 between the low-profile infusion set 80 and tube set connection element 82. In doing so, a tube set 84 can be attached to the tube set connection element 82 and placed in fluid communication with the infusion set 80, but wherein the infusion set 80 is isolated from movement of the tube set 84 by the tortuous pathed or zigzag patterned portion of adhesive base 88 and tubing 86.

As noted above, the ability to combine such elements, either integrated with one another, stored with one another, or installed with one another, can simplify use. In these and other exemplary embodiments of the present invention, such devices can further benefit from the provision of other exemplary strain relief elements. For example, flexible joints or materials in the tube set connections can be used in place of elements that secure the tube at a position away from the set, or which secure extra portions of tubing to absorb movement. For example, FIG. 5 is a perspective view of an exemplary concertina-type strain relief in accordance with an embodiment of the present invention.

Figure 5:
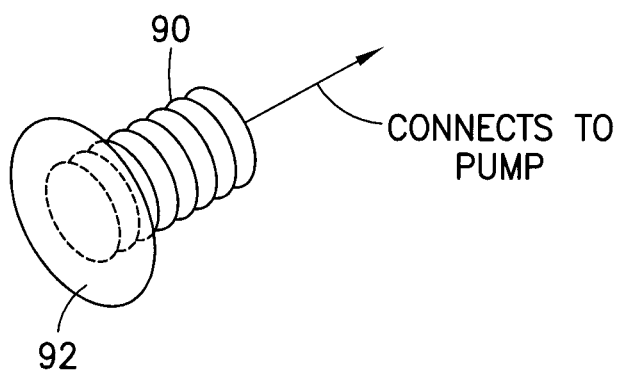
FIG. 5 is a perspective view of an exemplary concertina-type strain relief in accordance with an embodiment of the present invention.

In FIG. 5, a flexible joint 90 is provided at some point along a tube set connection, at the infusion set, infusion pump or somewhere therebetween. The flexible joint 90 can be configured as a concertina (i.e., bellows), constructed of silicone or similar materials, to allow movement between one end and another end. In an exemplary embodiment, the flexible joint 90 can be incorporated into the infusion set itself and can include an adhesive patch 92 to be secured at an infusion site.

Figure 6:
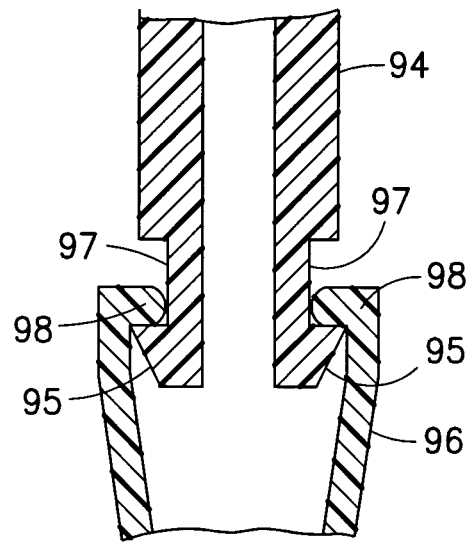
FIG. 6 is a perspective view of an exemplary two-part strain relief in accordance with an embodiment of the present invention.

FIG. 6 is a cross-sectional view of another exemplary flexible joint that is provided at some point along a tube set connection, at the infusion set, infusion pump or somewhere therebetween. The flexible joint of FIG. 6 can be configured as a male end configured to be slidably captured within a female end to allow movement between one end and another end while maintaining a seal between each. The flexible joint is configured as a two-part, connectable catheter to allow movement between a male end 94 and an opposite female end 96. The female end 96 comprises an opening surrounded by detents 98. The detents 98 are deflectable by engagement with the male end 94. Specifically, the male end 94 can comprise inclines 95 and a recess 97 to slidably capture the detents 98 of the female end 96, and permit a degree of movement while providing a seal between each. The detents 98 can be strongly biased toward the recess 97 when assembled to provide a fluid-tight seal between ends 94 and 96.

As noted above, the infusion pump is another part of the assembly of infusion set elements which work together to deliver insulin or other medicament to an infusion site. In exemplary embodiments of the present invention, such devices can benefit from the provision of a medicament pump that is configured to pump in both directions, such as a peristaltic pump or a diaphragm pump. The infusion set and pump can then be configured to use the pump to evacuate the reservoir, ideally a flexible reservoir, pressurize the insulin vial or other medicament supply, and draw fluid in from the insulin vial to the reservoir. FIGS. 7A to 7E, and FIGS. 8A to 8D, are views of an infusion system incorporating a linear peristaltic pump as another part of an assembly of infusion set elements which work together to deliver insulin or other medicament to an infusion site.

FIGS. 7A to 7E are block diagrams of an infusion system incorporating a linear peristaltic pump that can be combined with an infusion set and used to deliver insulin or other medicament to an infusion site, and FIGS. 8A to 8D are perspective views of an exemplary use of such an infusion system. A peristaltic pump is a positive displacement pump for pumping fluids using a flexible tube which is periodically compressed and released thereby forcing fluid to be pumped through the tube. As shown in FIG. 7A, an infusion set can comprise a reservoir 102, vial 104 and introducer needle, soft catheter, or in-dwelling cannula 106. The reservoir 102, vial 104 and introducer needle, soft catheter, or in-dwelling cannula 106 can be connected via a valve 108. A linear peristaltic pump 100 can be provided at any convenient position such as, for example, between the reservoir 102 and the valve 108.

In FIG. 7B, the linear peristaltic pump 100 can be operated to draw air up into the introducer needle, soft catheter, or in-dwelling cannula 106 and into the reservoir 102. When a vial 104 is coupled to the valve 108 in FIG. 7C, the valve 108 and linear peristaltic pump 100 can then be operated to force the air from the reservoir 102 into the vial 104 to pressurize the vial 108. The valve 108 and linear peristaltic pump 100 can then be operated to pump medicament from the pressurized vial 104 to fill the reservoir 102 in FIG. 7D. The valve 108 and linear peristaltic pump 100 can then be operated to pump medicament from the reservoir 102 to the introducer needle, soft catheter, or in-dwelling cannula 106 in FIG. 7E. FIGS. 8A to 8D are perspective views of an exemplary use of such a linear peristaltic pump.

FIG. 8A illustrates an assembly 110 containing therein one or more of the linear peristaltic pump 100, reservoir 102, introducer needle, soft catheter, or in-dwelling cannula 106 and valve 108. In FIG. 8A the linear peristaltic pump 100 is used to draw air into the reservoir 102. Once the vial 104 is connected as shown in FIG. 8B the linear peristaltic pump 100 is used to pressurize the vial 104 then fill the reservoir 102 from the now pressurized vial 104. Once the vial 104 is removed as shown in FIG. 8C, the linear peristaltic pump 100 is used to pump the content of the reservoir 102 to the introducer needle, soft catheter, or in-dwelling cannula 106 as shown in FIG. 8D.

A Piezo device can also be utilized as part of an infusion pump, infusion set, or as a separate component for use with either an infusion pump or infusion set. For example, a Piezo-electric pump can be used to move medicament, and can also be used to vibrate an introducer needle, catheter, or in-dwelling cannula on insertion to prevent tenting of the skin. The vibrations caused by the Piezo device or Piezo-electric pump help the edges of the introducer needle, catheter, or in-dwelling cannula to cut tissue, causing a smoother entry of the introducer needle, catheter, or in-dwelling cannula into the tissue. For example, FIGS. 9A to 9C are enlarged perspective views of an infusion system incorporating a Piezo device that can be used to deliver insulin or other medicament to an infusion site in accordance with such an embodiment of the present invention.

Figure 9A:
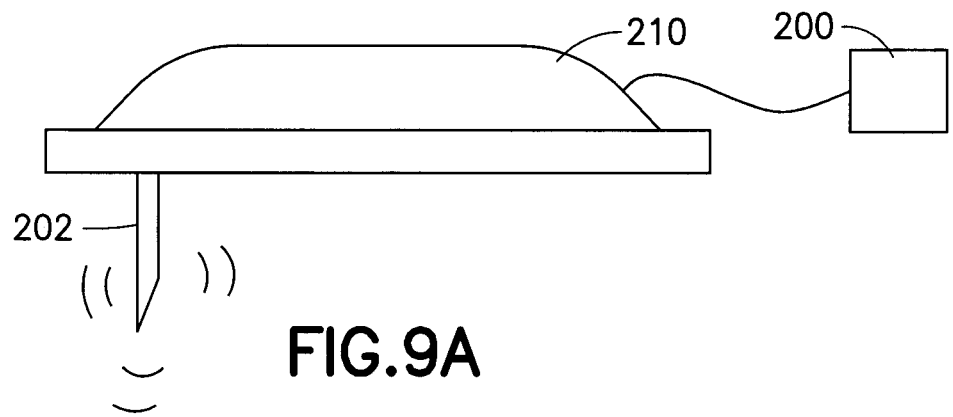
FIGS. 9A to 9C are views of an infusion system incorporating a Piezo device that can be used to deliver insulin or other medicament to an infusion site in accordance with an embodiment of the present invention.
Figure 9B:
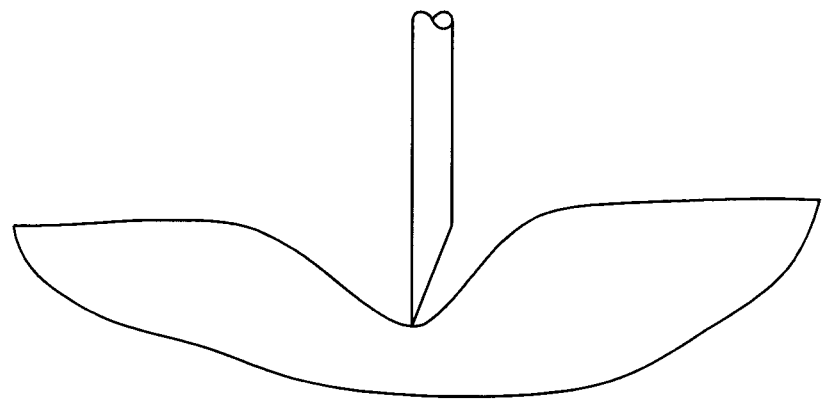
Figure 9C:
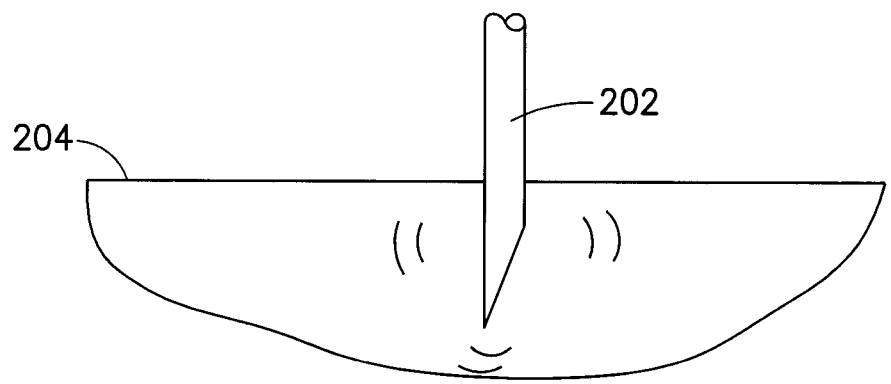

FIG. 9A illustrates an infusion set 210 coupled to a Piezo device 200 that can be incorporated with, or serve as an infusion pump, or which can be incorporated with, or serve as an infusion set, or as a separate component for use with either an infusion pump or infusion set. A Piezo device is one that incorporates materials that change shape when a voltage is applied, such that the changing shapes can be used to perform a number of tasks. In this case, the Piezo device 200 can be constructed to operate as a very small pump, or to create slight vibrations when controlled to do so. In the exemplary embodiment, the Piezo device 200 can be constructed to provide a communicable vibration to the infusion set 210 and specifically, to the introducer needle, catheter, or in-dwelling cannula 202 of the infusion set 210. If a Piezo device 200 is utilized as part of an infusion patch pump or other infusion set, the Piezo motion can be used to enhance the puncture characteristics of the introducer needle, catheter, or in-dwelling cannula 202 into the surface 204 of the skin as shown in FIG. 9C thereby, for example, reducing tenting of the skin surface as shown FIG. 9B of a conventional insertion without vibration, which can be beneficial to the shallow placement of an introducer needle, catheter, or in-dwelling cannula. The infusion pump can incorporate such features to aid needle, catheter, or in-dwelling cannula insertion or improve pump characteristics. Still other features that can be incorporated into such an infusion system or pump include a heat exchanger (not shown) to maintain the temperature of the insulin or other contents, or cool the insulin or other components of the pump if the temperature rises above a set point.

In other exemplary embodiments, actual pump functions can be performed by modifying elements of the infusion system. For example, FIGS. 10A and 10B are views of a collapsible cylinder or reservoir that can be used to deliver insulin or other medicament to an infusion site in accordance with an embodiment of the present invention.

FIGS. 10A and 10B are cross-sectional views of a collapsible cylinder or reservoir 220 that can be used to deliver insulin or other medicament to an infusion site. In the embodiment of FIGS. 10A and 10B, an insulin vial, cartridge, reservoir or similar element can be constructed from a portion of tubing, such as a portion of the infusion set tubing or other medical grade tubing, preferably one having a high elongation characteristic (e.g., elongation capability of 200% to 800%). In an example shown in FIGS. 10A and 10B, for a dimension X, the tubing can be expanded to a length 6× to create a chamber of length 4×, and when released, the tubing can contract to a length 2×, substantially collapsing the entire chamber therein. To do so, the tube segment can be filed with medicament to force the tube segment 222 into an elongated shape as shown in FIG. 10A. The tube segment can be closed at either end with contoured walls 224 and 226 to reduce dead space when contracted. The filling can further create a tensile force sufficient to deliver the content when released and the tube segment 224 contracts due to its high elongation characteristic as shown in FIG. 10B. The content can be delivered through a cannula or further tube segment 228. In yet another exemplary embodiment, the tube segment can be disposed within a reservoir chamber. For example, FIG. 11A is a cross-sectional view of another collapsible cylinder or reservoir disposed within a structured chamber that can be used to deliver insulin or other medicament to an infusion site in accordance with an embodiment of the present invention.

Figure 11A:
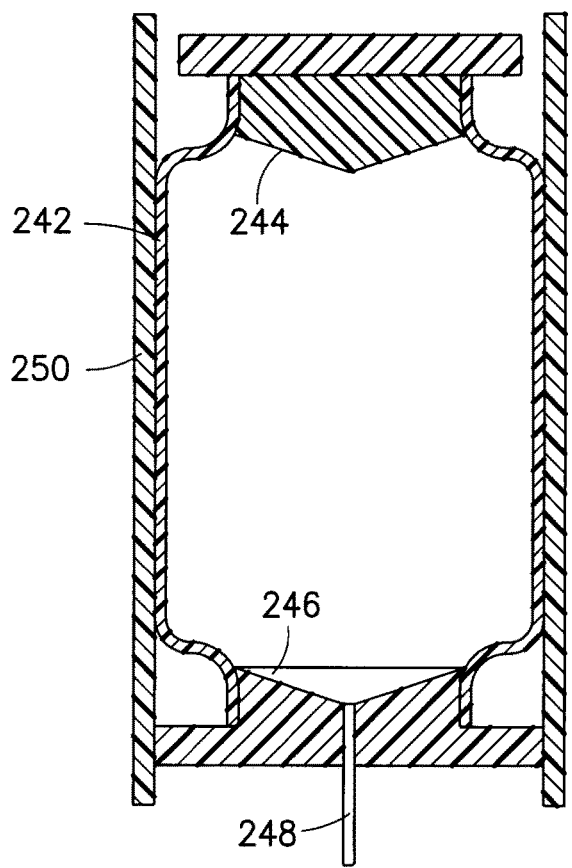
FIGS. 11A and 11B are views of another tube element that can be used to deliver insulin or other medicament to an infusion site in accordance with an embodiment of the present invention.
Figure 11B:
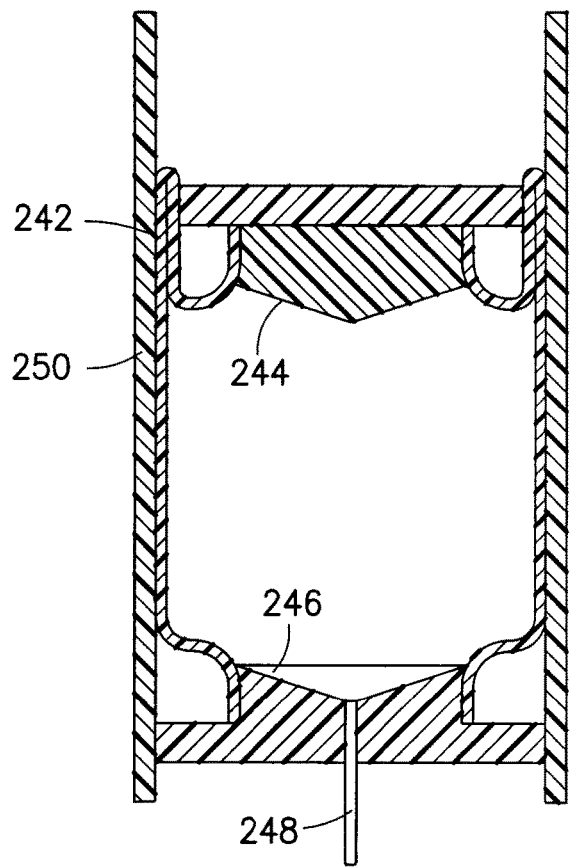

FIGS. 11A and 11B are enlarged cross-sectional views of a collapsible cylinder or reservoir 240 disposed within a structured chamber that can be used to deliver insulin or other medicament to an infusion site. In the embodiment of FIG. 11A, an insulin vial, cartridge, reservoir or similar element is constructed from a portion of tubing 242, such as a portion of the tube set tubing or other medical grade tubing, preferably one having high expansion characteristic. The tube segment can be disposed within a housing 250 or other tube segment. Accordingly, the tube segment 242 can be filled with medicament to force the tube segment 242 into an expanded shape as shown. The tube segment 242 can be closed at either end with contoured walls 244 and 246 to reduce dead space when contracted. At least one of the contoured walls, such as contoured wall 244 in FIG. 11A can be provided with spaces or gaps where slidably contacting the housing 250 to provide clearance for folding sections of the tube segments 242 during collapse as shown in FIG. 11B. The filling can create a tensile force sufficient to deliver the content when released and the tube segment 242 contracts due to the high expansion characteristic and can fold into gaps provided in the contoured wall 244. The content can be delivered through a cannula or further tube segment 248.

The housing 250 can be sized to prevent contact with the expanding tube segment 242, or the outer diameter of the tube segment 242 can be lubricated to allow the surface of the tube segment 242 to slide freely across the inner surface of the housing 250. In yet another exemplary embodiment, one or more of the moving wall segments in the reservoir can comprise a lubrication membrane to provide lubrication for moving elements. For example, FIGS. 12A to 12D are cross-sectional views of such an embodiment that can be used to deliver insulin or other medicament to an infusion site in accordance with an embodiment of the present invention.

FIG. 12A is a cross-sectional view of a reservoir housing 300 that comprises one or more moving wall segments such as the plunger or stopper 302 that includes a lubrication membrane 304 (i.e., an oil impregnated membrane) between stiff elastomer walls 306 and 308. In the exemplary embodiment shown, the moving wall segment 302 is a plunger or stopper of a syringe or reservoir, and provides lubrication features therein such that the remainder of the syringe or reservoir does not require a separate lubricating coating on interior walls. By impregnating O-rings, washers, disks or other porous membranes 304 in the plunger or stopper 302 with a lubricant, and designing the plunger or stopper 302 to release the lubricant of the porous membranes 304 only when dispense/inject forces are present, the moving wall of the syringe or reservoir is lubricated, but insulin or other medicament contents are not exposed to the lubricant of the porous membrane 304 preferably at all, and in other cases are not exposed to the lubricant of the porous membrane 304 until infusion begins, and exposure at that time is minimal throughout the infusion process.

To do so, the lubrication membrane 304 and elastomer walls 306 and 308 are configured to be driven along a central axis by a syringe engagement 310 when filling from a vial 312 as shown in FIG. 12A. The syringe engagement 310 drives the plunger or stopper 302 without compressing the lubrication membrane 304, so that the syringe can be utilized for filling or emptying the syringe from the vial 312. The syringe engagement 310 can be removed as shown in FIG. 12B, and replaced with a pump engagement 314 as shown in FIG. 12C. The pump engagement 314 is not configured to drive the plunger or stopper 302 along a central axis as with the syringe engagement 310, but provides wider contact elements 316 extending beyond the central axis. In doing so, the wider contact elements 316 of the pump engagement 314 bear on the outer diameter of the elastomer wall 308 of the plunger or stopper 302, deflecting the wall 308 into the membrane 304, compressing the lubrication membrane 304 and releasing lubrication between the outer diameter of the plunger and the inner diameter of the reservoir as shown in FIG. 12D. Accordingly, the lubricant of the lubrication membrane 304 is only dispensed when dispense/injection forces are present, such that the insulin or other medicament contents will not be exposed to the lubricant of the porous membrane 304 preferably at all, and in other cases will not be exposed to the lubricant of the porous membrane 304 until infusion begins and exposure at that time will be minimal throughout the infusion process. These embodiments described above incorporate pump features that benefit medicament or pumping operations. However, in yet other exemplary embodiments, the pump can incorporate features unrelated to pumping, but which still form part of an assembly of infusion set elements which work together to deliver insulin or other medicament to an infusion site. As an example, FIG. 13 shows a tubing recoiler utilized as part of an infusion pump.

Figure 13:
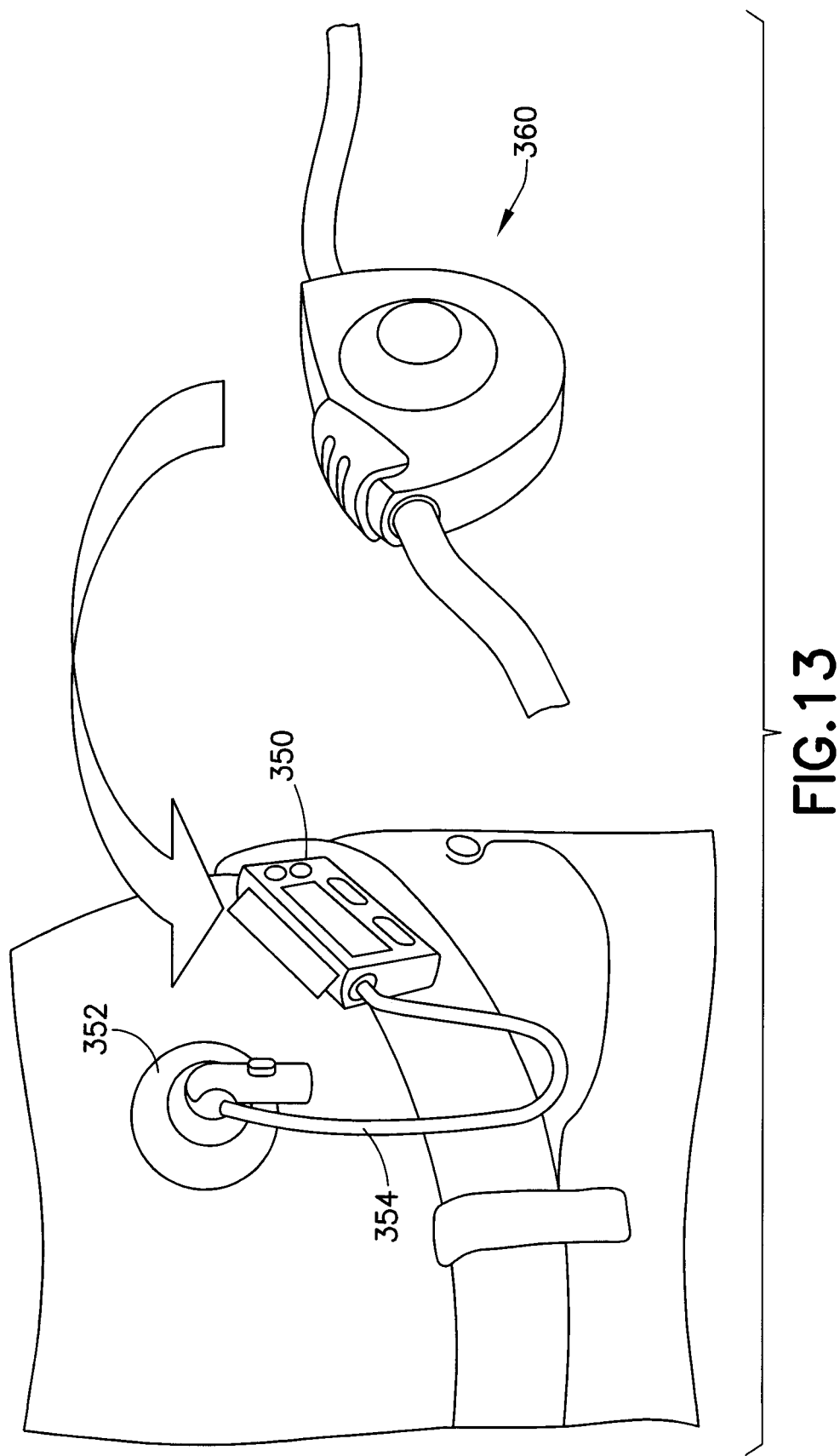
FIG. 13 is a view of a tubing recoiler utilized as part of an infusion pump and infusion set connection in accordance with an embodiment of the present invention.

FIG. 13 is a perspective view of a tubing recoiler utilized as part of an infusion pump. An infusion pump 350 is shown coupled with an infusion set 352 via a length of tube 354. However, excess tube between the infusion pump 350 and the infusion set 352 can be subject to interference and transfer undesired movement to the infusion set 352 through contact. Accordingly, it is desirable to minimize the length of tubing 354, but provide sufficient length to ease use and placement of the infusion set 352. In other systems, a separate tubing recoiler 360 has been provided to serve this function. However, the provision of such a separate element requires the user to carry, install and manage the separate component. Accordingly, exemplary embodiments of the present invention incorporate the separate tubing recoiler into the infusion pump 350.

Specifically, the pump 350 integrates the tubing and recoiler to automatically recoil excess tubing via a spring mechanism or otherwise, and dispense tubing in a reverse manner, so that another separate device is not required to manage excess tubing. The tubing 354 connecting the insulin supply and pump 350 to the infusion set 352 can be packaged on a spring-loaded circular reel disposed within the pump 350. The tubing 354 can enter and exit the pump 350 and wrap about a spring mechanism. Since the construction of a spring-loaded circular reel is known to those skilled in the art, additional features of such a reel are omitted for clarity. The circular reel can further comprise a catch/latch mechanism as known to those skilled in the art such that pulling the tube 354 a first time feeds a length of tube, and a catch is provided to prevent a reverse spring-urged action. Upon pulling the tube 354 a second time, the catch is released so that the reverse spring-urged action urges the tube 354 back into the pump 350. In doing so, the reel device allows slack tubing to be fed out precisely, with spring resistance maintaining the excess tubing rolled up and stored. The locking catch or latch can be provided to allow the user to prevent inadvertent retraction or extension once a satisfactory length of tubing has been deployed.

In exemplary embodiments of the present invention, the housings, hubs and other elements of the infusion system can be constructed of molded plastic materials, polycarbonate, thermoplastic polymers such as polyethylene terephthalate (PET and PETG), or similar materials. Springs and introducer needles can be constructed of stainless steel or similar materials. Although the embodiments described above are dimensioned and configured for subcutaneous injections, they can also be used for other types of injections, such as intradermal or intramuscular injections.

Further, features such as 360 degree rotation or partial rotation, line set connection, septum location, and so on, can be located in the strain relief rather than in the infusion set base or hub to which the Teflon cannula or catheter is secured. The strain relief can then be used to minimize the effect of line set movement or tugging, and motion that occurs at the catheter or cannula. This includes (1) tugging on the line set, as occurs when the line set catches on a door knob or other object and exerts a force to pull the infusion set from the skin, and (2) forces applied directly to the infusion hub, e.g. the patient or infusion set bumps into an object and a force is applied to the exterior of the infusion set, or the patient rolls over during sleep.

Further, one or more of the exemplary embodiments of the present invention can be provided with a skin contacting adhesive layer and backing. Precise insertion is achieved by first removing an adhesive cover of the adhesive layer, and then adhesively securing the infusion set hub to the infusion site via the adhesive, which permits the user to activate the inserter or place the catheter as described above at the proper alignment. Following adhesive attachment, the introducer needle, in-dwelling cannula and/or catheter is driven into the skin surface at a controlled high rate of speed to minimize the risk of misalignment at insertion. Further, the adhesive at or very near the insertion site secures the skin surface and minimizes tenting of the skin surface during insertion.

In current infusion sets which deliver insulin or other medicament to the subcutaneous layer, the catheter is usually not isolated from any undesired outside forces, which may cause pain when translated to the catheter which then moves within the skin. Also, other devices face problems of premature or unintended catheter removal when the device is bumped, if the catheter is not isolated from the outside forces. In the exemplary embodiments of the present invention, the catheter can be isolated from outside forces by at least one flexible or resilient feature or strain relief.

Although only a few exemplary embodiments of the present invention have been described in detail above, those skilled in the art will readily appreciate that many modifications are possible in the exemplary embodiments without materially departing from the novel teachings and advantages of this invention. Accordingly, all such modifications are intended to be included within the scope of the appended claims and their equivalents.

The invention claimed is:

1. An apparatus for an infusion set and infusion pump comprising at least one tube having a distal end secured to said infusion set and a proximal end secured to said infusion pump, the apparatus comprising:
   a first tube segment comprising an opening and a shoulder disposed about an inner circumference of said opening; and
   a second tube segment comprising a detent for slidably capturing said shoulder of said first tube segment, wherein a distal end of said second tube segment is tapered to facilitate entry into said opening of said first tube segment, and said detent comprises an untapered annular surface to prevent removal of said distal end of said second tube segment from said opening of said first tube segment;
   wherein said detent of said second tube segment is biased to create a seal with said shoulder of said first tube segment.

2. An apparatus for an infusion set, the infusion set comprising at least one of a reservoir, an introducer needle, a catheter and a bellows-shaped tube segment, the apparatus comprising a pump integrated with said infusion set, wherein said pump comprises a linear peristaltic pump adapted to pump in both a first direction and a second direction that is opposite to the first direction, wherein said linear peristaltic pump is configured to transfer content between a vial and said reservoir via the bellow-shaped tube segment by pumping in said first direction, and to transfer content between said reservoir and said catheter by pumping in said second direction.

3. An apparatus as claimed in claim 2, wherein said pump comprises an elongated tube segment, wherein said tube segment can be elongated to a first filled dimension and contract to a second empty dimension.

4. An apparatus as claimed in claim 2, wherein said pump comprises an expandable tube segment, wherein said tube segment can be expanded to a first filled dimension and contract to a second empty dimension.

5. An apparatus as claimed in claim 2, further comprising a Piezoelectric element configured to communicate a vibration to at least one of said introducer needle and catheter.

6. An apparatus as claimed in claim 2, wherein said pump further comprises a tube reel configured to store tubing in a substantially circular manner.

7. An apparatus as claimed in claim 2, wherein said reservoir comprises:
   a plunger comprising a lubrication membrane disposed between a first and second elastomer membrane, wherein said elastomer membrane is configured to compress said lubrication membrane when delivering medicament of said reservoir.

8. An apparatus as claimed in claim 7, wherein said compression of said lubrication membrane releases a lubricant between said plunger and said reservoir when delivering medicament of said reservoir.

* * * * *